United States Patent [19]
Duong et al.

[11] Patent Number: 6,057,113
[45] Date of Patent: May 2, 2000

[54] MOUSE INTEGRIN SUBUNITS

[75] Inventors: Le T. Duong, Jenkintown; Gideon A. Rodan, Bryn Mawr; Elka M. Nutt, Lansdale, all of Pa.

[73] Assignee: Merck & Co., Inc., Rahway, N.J.

[21] Appl. No.: 09/218,242

[22] Filed: Dec. 22, 1998

Related U.S. Application Data

[62] Division of application No. 08/960,387, Oct. 29, 1997, Pat. No. 5,895,754, which is a division of application No. 08/700,253, Aug. 20, 1996, abandoned.
[60] Provisional application No. 60/003,020, Aug. 31, 1995.
[51] Int. Cl.⁷ .................................................. C07K 14/715
[52] U.S. Cl. ............................. 435/7.1; 530/395; 436/501
[58] Field of Search ............................ 530/395; 436/501; 435/7.1

[56] References Cited

U.S. PATENT DOCUMENTS 5,391,704  2/1995  McMillan et al. .
5,661,005  8/1997  Shattil et al. .

OTHER PUBLICATIONS

Tang, D. G. et al. Activation of Microvascular Endothelium . . . Cancer Research 54, 1119–1129, Feb. 15, 1994.
Cieutat, A.M. et al. Biochem. Biophys. Res. Comm. vol. 193, No. 2, pp. 771–778 (1993).
Djaffar, I. et al. Biochem J., vol. 300, pp. 69–74 (1994).
Fitzgerald, L.A. et al. J. Biol. Chem. vol. 262, No. 9, pp. 3936–3939, (1987).
Van Kuppevelt, T.H.MS.M. et al. Proc. Natl. Acad. Sci., USA, vol. 86, No. 14, pp. 5415–5418 (1989).

*Primary Examiner*—Christina Y. Chan
*Assistant Examiner*—Amy DeCloux
*Attorney, Agent, or Firm*—Anna L. Cocuzzo; Joanne M. Giesser; Jack L. Tribble

[57] ABSTRACT

The full-length mouse β3 integrin has been cloned and sequenced. A new form of β3 integrin (β3-trunc also been cloned and sequenced.

4 Claims, 20 Drawing Sheets

```
  1  ATAACAATTT CACACAGGAA ACAGCTATGA CCATGATTAC GCCAAGCTCG
 51  AAATTAACCC TCACTAAAGG GAACAAAAGC TGGAGCTCCA CCGGTGGCGG
101  CCGCTCTAGA ACTAGTGGAT CCCCCGGGCT GCAGGAATTC GCGCCGTCGA
151  CGCGGCGGAC AGGATGCGAG CGCAGTGGCC GGGACAACTC TGGGCCGCTC
201  TGCTGGCGCT GGGGGCGCTG GCGGGCGTTG TTGTTGGAGA GTCCAACATC
251  TGTACCACAC GAGGCGTGAA CTCCTGCCAG CAGTGTCTGG CTGTGAGTCC
301  TGTGTGTGCC TGGTGCTCAG ATGAGACTTT GTCTCAGGGC TCACCCCGAT
351  GTAACCTGAA GGAGAACCTG CTGAAGGACA ATTGTGCTCC AGAGTCTATT
401  GAGTTCCCAG TCAGTGAGGC CCAGATCCTG GAGGCTAGGC CACTCAGCAG
451  CAAGGGCTCT GGAAGCAGCG CCCAGATCAC TCAAGTCAGC CCTCAGAGGA
501  TTGCCCTTCG ACTACGGCCA GATGATTCGA AGATCTTCTC ACTTCAAGTG
551  CGGCAGGTGG AGGATTACCC CGTGGACATC TACTACTTGA TGGACCTGTC
601  TTTCTCCATG AAGGATGATC TGTCCAGCAT CCAGACCCTG GGTACCAAGT
651  TGGCCCTCTC A GATGCGCAAG CTTACTAGCA ACCTTCGGAT TGGCTTTGGG
```

FIG. 1A

```
 701   GCCTTCGTGG  ACAAGCCTGT  ATCGCCGTAC  ATGTACATCT  CCCCACCACA
 751   GGCAATCAAA  AACCCCTGTT  ACAATATGAA  GAATGCCTGC  TTGCCCATGT
 801   TTGGCTACAA  ACACGTGCTG  ACGCTAACCG  ACCAGGTGTC  CCGCTTCAAT
 851   GAAGAAGTGA  AGAAACAGAG  CGTGTCCCGT  AATCGAGATG  CCCCAGAGGG
 901   CGGCTTTGAC  GCCATCATGC  AGGCTACAGT  ATGTGATGAA  AAAATTGGCT
 951   GGAGGAATGA  CGCATCCCAT  TTGCTAGTGT  TTACCACGGA  TGCCAAGACC
1001   CATATTGCCC  TGGATGGAAG  ACTGGCAGGC  ATTGTCCTGC  CCAATGATGG
1051   GCACTGTCAC  ATTGGCACCG  ACAACCACTA  CTCTGCCTCC  ACTACCATGG
1101   ACTACCCATC  TCTGGGGCTG  ATGACTGAGA  AACTATCCCA  GAAAAACATT
1151   AACTTGATCT  TTGCAGTGAC  TGAAAATGTC  GTCAGCCTTT  ACCAGAATTA
1201   TAGTGAGCTC  ATTCCTGGGA  CCACAGTGGG  AGTCCTGTCT  GATGACTCAA
1251   GCAACGTCCT  CCAGCTGATT  GTTGATGCTT  ACGGGAAAAT  CCGCTCTAAA
1301   GTGGAGCTGG  AAGTACGTGA  CCTGCCGGAA  GAACTGTCAC  TGTCCTTCAA
1351   TGCCACCTGC  CTCAACAACG  AGGTTATCCC  GGGCCTCAAG  TCTTGTGTGG
```

FIG. 1B

```
1401  GCCGCAAGAT  TGGAGACACG  GTGAGCTTTA  GTATCGAGGC  CAAGGTGCGT
1451  GGCTGCCCCC  AGGAGAAGGA  GCAGTCTTTC  ACTATCAAGC  CTGTGGGCTT
1501  TAAGGACAGC  CTCACCGTCC  AGTGACCTT   CGACTGTGAC  TGTGCCTGCC
1551  AGGCCTTTGC  CCAGCCTTCC  AGCCCACGCT  GCAACAATGG  GAACGGGACT
1601  TTTGAGTGTG  GGGTGTGCCG  CTGTGACCAG  GGCTGGCTGG  GGTCCATGTG
1651  TGAGTGCTCT  GAGGAGGATT  ACCGACCCTC  TCAGCAGGAA  GAGTGCAGCC
1701  CCAAGGAGGG  CCAGCCCATC  TGCAGCCAGC  GGGAGAGTG   CCTCTGTGGC
1751  CAGTGTGTCT  GCCATAGCAG  CGACTTCGGC  AAGATCACTG  GCAAGTACTG
1801  TGAGTGCGAT  GACTTCTCCT  GCGTCCGCTA  CAAAGGGGAG  ATGTGTTCCG
1851  GCCATGGGCA  ATGTAACTGT  GGGGACTGCG  TGTGTGACTC  GGACTGGACT
1901  GGCTACTACT  GCAACTGTAC  TACACGCACT  GACACCTGCA  TGTCCACCAA
1951  TGGGCTGCTG  TGCAGCGGCC  GGGGCAACTG  CGAGTGCGGC  AGCTGTGTGT
2001  GCGTCCAGCC  AGGCTCCTAT  GGAGACACCT  GTGAGAAGTG  CCCCACCTGC
2051  CCAGATGCCT  GCTCCTTTAA  GAAGGAGTGT  GTGGAGTGTA  AGAAGTTCAA
```

FIG. 1C

```
2101  CCGGGGAACG  CTCCATGAAG  AAAACACCTG  CAGCCGCTAC  TGCCGGGATG
2151  ACATCGAGCA  GGTGAAAGAG  CTGACGGATA  CTGGCAAAAA  CGCCCGTGAAT
2201  TGTACCTACA  AGAACGAGGA  TGACTGTGTC  GTCAGATTCC  AGTACTACGA
2251  AGACACCAGT  GGGAGGGCAG  TCCCTCTATGT  GGTGGAAGAG  CCTGAGTGTC
2301  CCAAGGGTCC  TGATATCCTG  GTGGTACTGC  TGTCAGTGAT  GGGGGCCATC
2351  CTGCTCATTG  GCCTTGCTAC  TCTGCTCATC  TGGAAGCTAC  TCATCACCAT
2401  CCATGACCGG  AAGGAATTTG  CTAAATTTGA  GGAAGAACGA  GCCAGAGCTA
2451  AGTGGGACAC  AGCAAACAAC  CCGCTGTATA  AAGAGGCCAC  CTCCACCTTC
2501  ACCAATATCA  CGTACCGAGG  AACTTAATGA
```

FIG. 1D

```
  1  ATAACAATTT CACACAGGAA ACAGCTATGA CCATGATTAC GCCAAGCTCG
 51  AAATTAACCC TCACTAAAGG GAACAAAAGC TGGAGCTCCA CCGGTGGCGG
101  CCGCTCTAGA ACTAGTGGAT CCCCCGGGCT GCAGGAATTC GCGCCGTCGA
151  CGCGGGGGAC AGGATGCGAG CGCAGTGGCC GGGACAACTC TGGGCCGCTC
201  TGCTGGCGCT GGGGGCGCTG GCGGGGCGTTG TTGTTGGAGA GTCCAACATC
251  TGTACCACAC GAGGCGTGAA CTCCTGCCAG CAGTGTCTGG CTGTGAGTCC
301  TGTGTGTGCC TGGTGCTCAG ATGAGACTTT GTCTCAGGGC TCACCCCGAT
351  GTAACCTGAA GGAGAACCTG CTGAAGGACA ATTGTGCTCC AGAGTCTATT
401  GAGTTCCCAG TCAGTGAGGC CCAGATCCTG GAGGCTAGGC CACTCAGCAG
451  CAAGGGCTCT GGAAGCAGCG CCCAGATCAC TCAAGTCAGC CCTCAGAGGA
501  TTGCCCTTCG ACTACGGCCA GATGATTCGA AGATCTTCTC ACTTCAAGTG
551  CGGCAGGTGG AGGATTACCC CGTGGACATC TACTACTTGA TGGACCTGTC
601  TTTCTCCATG AAGGATGATC TGTCCAGCAT CCAGACCCTG GGTACCAAGT
651  TGGCCTCTCA GATGCGCAAG CTTACTAGCA ACCTTCGGAT TGGCTTTGGG
```

FIG. 2A

```
701   GCCTTCGTGG ACAAGCCTGT ATCGCCGTAC ATGTACATCT CCCCACCACA
751   GGCAATCAAA AACCCCTGTT ACAATATGAA GAATGCCTGC TTGCCCATGT
801   TTGGCTACAA ACACGTGCTG ACGCTAACCG ACCAGGTGTC CCGCTTCAAT
851   GAAGAAGTGA AGAAACAGAG CGTGTCCCGT AATCGAGATG CCCCAGAGGG
901   CGGCTTTGAC GCCATCATGC AGGCTACAGT ATGTGATGAA AAAATTGGCT
951   GGAGGAATGA CGCATCCCAT TTGCTAGTGT TTACCACGGA TGCCAAGACC
1001  CATATTGCCC TGGATGGAAG ACTGGCAGGC ATTGTCCCTGC CCAATGATGG
1051  GCACTGTCAC ATTGGCACCG ACAACCACTA CTCTGCCTCC ACTACCATGG
1101  ACTACCCATC TCTGGGGCTG ATGACTGAGA AACTATCCCA GAAAAACATT
1151  AACTTGATCT TTGCAGTGAC TGAAAATGTC GTCAGCCTTT ACCAGAATTA
1201  TAGTGAGCTC ATTCCTGGGA CCACAGTGGG AGTCCTGTCT GATGACTCAA
1251  GCAACGTCCT CCAGCTGATT GTTGATGCTT ACGGGAAAAT CCGCTCTAAA
1301  GTGGAGCTGG AAGTACGTGA CCTGCCGGAA GAACTGTCAC TGTCCTTCAA
1351  TGCCACCTGC CTCAACAACG AGGTTATCCC GGGCCTCAAG TCTTGTGTGG
```

FIG. 2B

```
1401  GCCGCAAGAT TGGAGACACG GTGAGCTTTA GTATCGAGGC CAAGGTGCGT
1451  GGCTGCCCCC AGGAGAAGGA GCAGTCTTTC ACTATCAAGC CTGTGGGCTT
1501  TAAGGACAGC CTCACCGTCC AGGTGACCTT CGACTGTGAC TGTGCCTGCC
1551  AGGCCCTTTGC CCAGCCTTCC AGCCCACGCT GCAACAATGG GAACGGGACT
1601  TTTGAGTGTG GGGTGTGCCG CTGTGACCAG GGCTGGCTGG GGTCCATGTG
1651  TGAGTGCTCT GAGGAGGATT ACCGACCCTC TCAGCAGGAA GAGTGCAGCC
1701  CCAAGGAGGG CCAGCCCATC TGCAGCCAGC GGGGAGAGTG CCTCTGTGGC
1751  CAGTGTGTCT GCCATAGCAG CGACTTCGGC CGTCCGCTA AAGATCACTG GCAAGTACTG
1801  TGAGTGCGAT GACTTCTCCT GCGTCCGCTA CAAAGGGGAG ATGTGTTCCG
1851  GCCATGGGCA ATGTAACTGT GGGGACTGCG TGTGTGACTC GGACTGGACT
1901  GGCTACTACT GCAACTGTAC TACACGCACT GACACCTGCA TGTCCACCAA
1951  TGGGCTGCTG TGCAGCGGCC GGGGCAACTG CGAGTGCGGC AGCTGTGTGT
2001  GCGTCCAGCC AGGCTCCTAT GGAGACACCT GTGAGAAGTG CCCCACCTGC
2051  CCAGATGCCT GCTCCTTTAA GAAGGAGTGT GTGGAGTGTA AGAAGTTCAA
```

FIG. 2C

```
2101  CCGGGGAACG CTCCATGAAG AAAACACCTG CAGCCGCTAC TGCCGGGATG
2151  ACATCGAGCA GGTGAAAGAG CTGACGGATA CTGGCAAAAA CGCCCGCGGC
2201  CGCGTCGACT GGAGACTCAC GGAGCATGAC ATACTCACCT GTCACCTATT
2251  TAGAAGACTG AGGCAGGAAG ATAAGTTTCT GGACAGCCTA GTCTGCATAA
2301  AGACCACCCT GTCTCAAAAA GCATAAAAGG GGCGTGGTGA ATGCCTGCTT
2351  AGCATATAGC CCTTGGTTGC AGGTAGTGCA GTACATAGGT GAAATCTGCC
2401  GCTACCTGCT GAGGCAGCCG GTTCGCGACG TGGAGCAGCG ACACCGCGTG
2451  CGCCTGGCCG CGGGTAATGG GCTGCGGCCA AGATCGGCGA GCCATCTGGG AGGAGTTCAC
2501  GCAGCGCTTC GGTGTGCCAC AGATCGGCGA GTTCTACGGC GCTACCGAGT
2551  GCAACTGAGC ATTGCCAACA TGGACGGCAA GGTTCGCAGC TGTGGGGTGC
2601  AGGCGGGCGC TGTCGGTTTC CTACGACACA AGAGCCTTCA GGCCGCCCTC
2651  ACCGCCGCTG TATTCACCCT AGTCGGCTC CTGCGGCTTC AACAGCCGTA
2701  TCCTCACGCA TGTGTACCCC ATCCGTCTGG TCAAGGTCAA TGAGGACACG
2751  ATGGAGCCAC TGCGGGACTC CGAGGGCCTC TGCATCCCGT GCCAGCCCGG
```

FIG. 2D

```
2801  TGAGTGTGGC CCTTGCCTGG TGCCTCGGGG AGCTAGAGTC CCCACGGCCC
2851  CCACACCCAC TCAGCTTGAG TGTCAACCTC CTTCCAGGGG AACCCGGCCT
2901  TTCGTGGGCC AGATCAACCA GCAGGACCCT CTGCGGCGTT TCGATGGTTA
2951  TGTTAGTGAC AGTGCCACCA ACAAGAAGAT TGCCCACAGC GTTTTCCGAA
3001  AGGCGATACG gCCTACCTCT CAGGTGCGGA CGCTCGTGGT CGTGGCTGGG
3051  CTGGCTGTCA GACTGCAAAG CCCGGTCCCA TCTGCCCCTC TTCCCTGCAG
3101  GTGACGTGCT AGTGATGGAC GAGCTGGGCT ACATGTATTT CCGTGACCGC
3151  AGCGGGGACA CCTTCCGCTG GCGCGGGAGA ACGTGTCCAA CCACGGAGT
3201  GAAGCCGGTG CTGAGCCGCC TACTGGGCCA GACGGACGTG GCTGTGTATG
3251  GGGTGGCTGT GCAGGCAAGC TGGGGACACA GGGTGGTTGT GGTGTGCAGG
3301  AGCCCCATGG AGTCCATCCA GAAGGGACCT GCAGTACAG TACCCGTGGG
3351  CCATGCACAA GGTGGAGAAC TGTGTTGCTG CTGACTGGGT GGGCACTGGG
3401  TTGGGAATCC ATCCACATTC CTAATATTGA ACTTCAGTCT GGGGACCCC
3451  TTCTCAGGAT CAGAAGGCTG AAAACAGGTC GACGCCGCCC GGAATTCGAT
3501  ATCAAGCTTA TCGATCC
```

FIG. 2E

| | | | | | |
|---|---|---|---|---|---|
| 1 | *QFHTGNSYD | HDYAKLEINP | H*REQKLELH | RWRPL*N*WI | PRAAGIRAVD |
| 51 | AADRMRAQWP | GQLWAALLAL | GALAGVVVGE | SNICTTRGVN | SCQQCLAVSP |
| 101 | VCAWCSDETL | SQGSPRCNLK | ENLLKDNCAP | ESIEFPVSEA | QILEARPLSS |
| 151 | KGSGSSAQIT | QVSPQRIALR | LRPDDSKIFS | LQVRQVEDYP | VDIYYLMDLS |
| 201 | FSMKDDLSSI | QTLGTKLASQ | MRKLTSNLRI | GFGAFVDKPV | SPYMYISPPQ |
| 251 | AIKNPCYNMK | NACLPMFGYK | HVLTLTDQVS | RFNEEVKKQS | VSRNRDAPEG |
| 301 | GFDAIMQATV | CDEKIGWRND | ASHLLVFTTD | AKTHIALDGR | LAGIVLPNDG |
| 351 | HCHIGTDNHY | SASTTMDYPS | LGLMTEKLSQ | KNINLIFAVT | ENVVSLYQNY |
| 401 | SELIPGTTVG | VLSDDSSNVL | QLIVDAYGKI | RSKVELEVRD | LPEELSLSFN |
| 451 | ATCLNNEVIP | GLKSCVGRKI | GDTVSFSIEA | KVRGCPQEKE | QSFTIKPVGF |
| 501 | KDSLTVQVTF | DCDCACQAFA | QPSSPRCNNG | NGTFECGVCR | CDQGWLGSMC |
| 551 | ECSEEDYRPS | QQEECSPKEG | QPICSQRGEC | LCGQCVCHSS | DFGKITGKYC |
| 601 | ECDDFSCVRY | KGEMCSGHGQ | CNCGDCVCDS | DWTGYYCNCT | TRTDTCMSTN |
| 651 | GLLCSGRGNC | ECGSCVCVQP | GSYGDTCEKC | PTCPDACSFK | KECVECKKFN |

FIG. 3A

```
 701  RGTLHEENTC SRYCRDDIEQ VKELTDTGKN ARGRVDWRLT EHDILTCHLF
 751  RRLRQEDKFL DSLVCIKTTL SQKA*KGRGE CLLSI*PLVA GSAVHR*NLP
 801  LPAEAAGSRR GAATPRAPGR G*WAAASHLG GVHAALRCAT DRRVLRRYRV
 851  QLSIANMDGK VRSCGVQAGA VGFLRHKSLQ AALTAAVFTL GRLLRLQQPY
 901  PHACVPHPSG QGQ*GHDGAT AGLRGPLHPV PAR*VWPLPG ASGS*SPHGP
 951  HTHSA*VSTS FQGNPAFRGP DQPAGPSAAF RWLC**QCHQ QEDCPQRFPK
1001  GDTAYLSGAD ARGRGWAGCQ TAKPGPICPS SLQVTC**WT SWATCISVTA
1051  AGTPSAGAGE RVQPRR*SRC *AAYWARRTW LCMGWLCRQA GDTGWLWCAG
1101  APWSPSRRDL QVQYPWAMHK VENCVAADWV GTGLGIHPHS *Y*TSVWGTP
1151  SQDQKAENRS TPPGIRYQAY RS
```

FIG. 3B

```
  1  *QFHTGNSYD HDYAKLEINP H*REQKLELH RWRPL*N*WI PRAAGIRAVD
 51  AADRMRAQWP GQLWAALLAL GALAGVVGE SNICTTRGVN SCQQCLAVSP
101  VCAWCSDETL SQGSPRCNLK ENLLKDNCAP ESIEFPVSEA QILEARPLSS
151  KGSGSSAQIT QVSPQRIALR LRPDDSKIFS LQVRQVEDYP VDIYYLMDLS
201  FSMKDDLSSI QTLGTKLASQ MRKLTSNLRI GFGAFVDKPV SPYMYISPPQ
251  AIKNPCYNMK NACLPMFGYK HVLTLTDQVS RFNEEVKKQS VSRNRDAPEG
301  GFDAIMQATV CDEKIGWRND ASHLLVFTTD AKTHIALDGR LAGIVLPNDG
351  HCHIGTDNHY SASTTMDYPS LGLMTEKLSQ KNINLIFAVT ENVVSLYQNY
401  SELIPGTTVG VLSDDSSNVL QLIVDAYGKI RSKVELEVRD LPEELSLSFN
451  ATCLNNEVIP GLKSCVGRKI GDTVSFSIEA KVRGCPQEKE QSFTIKPVGF
501  KDSLTVQVTF DCDCACQAFA QPSSPRCNNG NGTFECGVCR CDQGWLGSMC
551  ECSEEDYRPS QQEECSPKEG QPICSQRGEC LCGQCVCHSS DFGKITGKYC
601  ECDDFSCVRY KGEMCSGHGQ CNCGDCVCDS DWTGYYCNCT TRTDTCMSTN
651  GLLCSGRGNC ECGSCVCVQP GSYGDTCEKC PTCPDACSFK KECVECKKFN
```

FIG. 4A

701 RGTLHEENTC SRYCRDDIEQ VKELTDTGKN AVNCTYKNED DCVVRFQYYE
751 DTSGRAVLYV VEEPECPKGP DILVVLLSVM GAILIGLAT LLIWKLLITI
801 HDRKEFAKFE EERARAKWDT ANNPLYKEAT STFTNITYRG T**

FIG. 4B

```
      55
MRAQWPGQLWAALLALGALAGVVVGESNICTTRGVNSCQQCLAVSPVCAW 104

||||||||||||||||||||||||||||||||||||||||||||||||||
      55
MRAQWPGQLWAALLALGALAGVVVGESNICTTRGVNSCQQCLAVSPVCAW 104

105
CSDETLSQGSPRCNLKENLLKDNCAPESIEFPVSEAQILEARPLSSKGSG 154

||||||||||||||||||||||||||||||||||||||||||||||||||
      105
CSDETLSQGSPRCNLKENLLKDNCAPESIEFPVSEAQILEARPLSSKGSG 154

155
SSAQITQVSPQRIALRLRPDDSKIFSLQVRQVEDYPVDIYYLMDLSFSMK 204

||||||||||||||||||||||||||||||||||||||||||||||||||
      155
SSAQITQVSPQRIALRLRPDDSKIFSLQVRQVEDYPVDIYYLMDLSFSMK 204

205
DDLSSIQTLGTKLASQMRKLTSNLRIGFGAFVDKPVSPYMYISPPQAIKN 254

||||||||||||||||||||||||||||||||||||||||||||||||||
      205
DDLSSIQTLGTKLASQMRKLTSNLRIGFGAFVDKPVSPYMYISPPQAIKN 254

255
PCYNMKNACLPMFGYKHVLTLTDQVSRFNEEVKKQSVSRNRDAPEGGFDA 304

||||||||||||||||||||||||||||||||||||||||||||||||||
      255
PCYNMKNACLPMFGYKHVLTLTDQVSRFNEEVKKQSVSRNRDAPEGGFDA 304
```

FIG. 5A

```
    305
IMQATVCDEKIGWRNDASHLLVFTTDAKTHIALDGRLAGIVLPNDGHCHI 354

| | | | | | | | | | | | | | | | | | | | | | | | | | | | | | | | | | | | | | | | | | | | | | | | |
    305
IMQATVCDEKIGWRNDASHLLVFTTDAKTHIALDGRLAGIVLPNDGHCHI 354

355
GTDNHYSASTTMDYPSLGLMTEKLSQKNINLIFAVTENVVSLYQNYSELI 404

| | | | | | | | | | | | | | | | | | | | | | | | | | | | | | | | | | | | | | | | | | | | | | | | |
    355
GTDNHYSASTTMDYPSLGLMTEKLSQKNINLIFAVTENVVSLYQNYSELI 404

405
PGTTVGVLSDDSSNVLQLIVDAYGKIRSKVELEVRDLPEELSLSFNATCL 454

| | | | | | | | | | | | | | | | | | | | | | | | | | | | | | | | | | | | | | | | | | | | | | | | |
    405
PGTTVGVLSDDSSNVLQLIVDAYGKIRSKVELEVRDLPEELSLSFNATCL 454

455
NNEVIPGLKSCVGRKIGDTVSFSIEAKVRGCPQEKEQSFTIKPVGFKDSL 504

| | | | | | | | | | | | | | | | | | | | | | | | | | | | | | | | | | | | | | | | | | | | | | | | |
    455
NNEVIPGLKSCVGRKIGDTVSFSIEAKVRGCPQEKEQSFTIKPVGFKDSL 504

505
TVQVTFDCDCACQAFAQPSSPRCNNGNGTFECGVCRCDQGWLGSMCECSE 554

| | | | | | | | | | | | | | | | | | | | | | | | | | | | | | | | | | | | | | | | | | | | | | | | |
    505
TVQVTFDCDCACQAFAQPSSPRCNNGNGTFECGVCRCDQGWLGSMCECSE 554
```

FIG. 5B

```
        555
EDYRPSQQEECSPKEGQPICSQRGECLCGQCVCHSSDFGKITGKYCECDD 604
        |||||||||||||||||||||||||||||||||||||||||||||||||
        555
EDYRPSQQEECSPKEGQPICSQRGECLCGQCVCHSSDFGKITGKYCECDD 604

605
FSCVRYKGEMCSGHGQCNCGDCVCDSDWTGYYCNCTTRTDTCMSTNGLLC 654
        |||||||||||||||||||||||||||||||||||||||||||||||||
        605
FSCVRYKGEMCSGHGQCNCGDCVCDSDWTGYYCNCTTRTDTCMSTNGLLC 654

655
SGRGNCECGSCVCVQPGSYGDTCEKCPTCPDACSFKKECVECKKFNRGTL 704
        |||||||||||||||||||||||||||||||||||||||||||||||||
        655
SGRGNCECGSCVCVQPGSYGDTCEKCPTCPDACSFKKECVECKKFNRGTL 704

705
HEENTCSRYCRDDIEQVKELTDTGKNAVNCTYKNEDDCVVRFQYYEDTSG 754
        |||||||||||||||||||||||||           .| :.. |..
        705
HEENTCSRYCRDDIEQVKELTDTGKNA.........RGRVDWRLTEHDIL 745

755 RAVLYVVEEPECPKGPDILVVLLSVMGA 782
            .|:    .| .|  |  ||.:  ..::.
        746 TCHLFRRLRQE.DKFLDSLVCIKTTLSQ 772
```

FIG. 5C

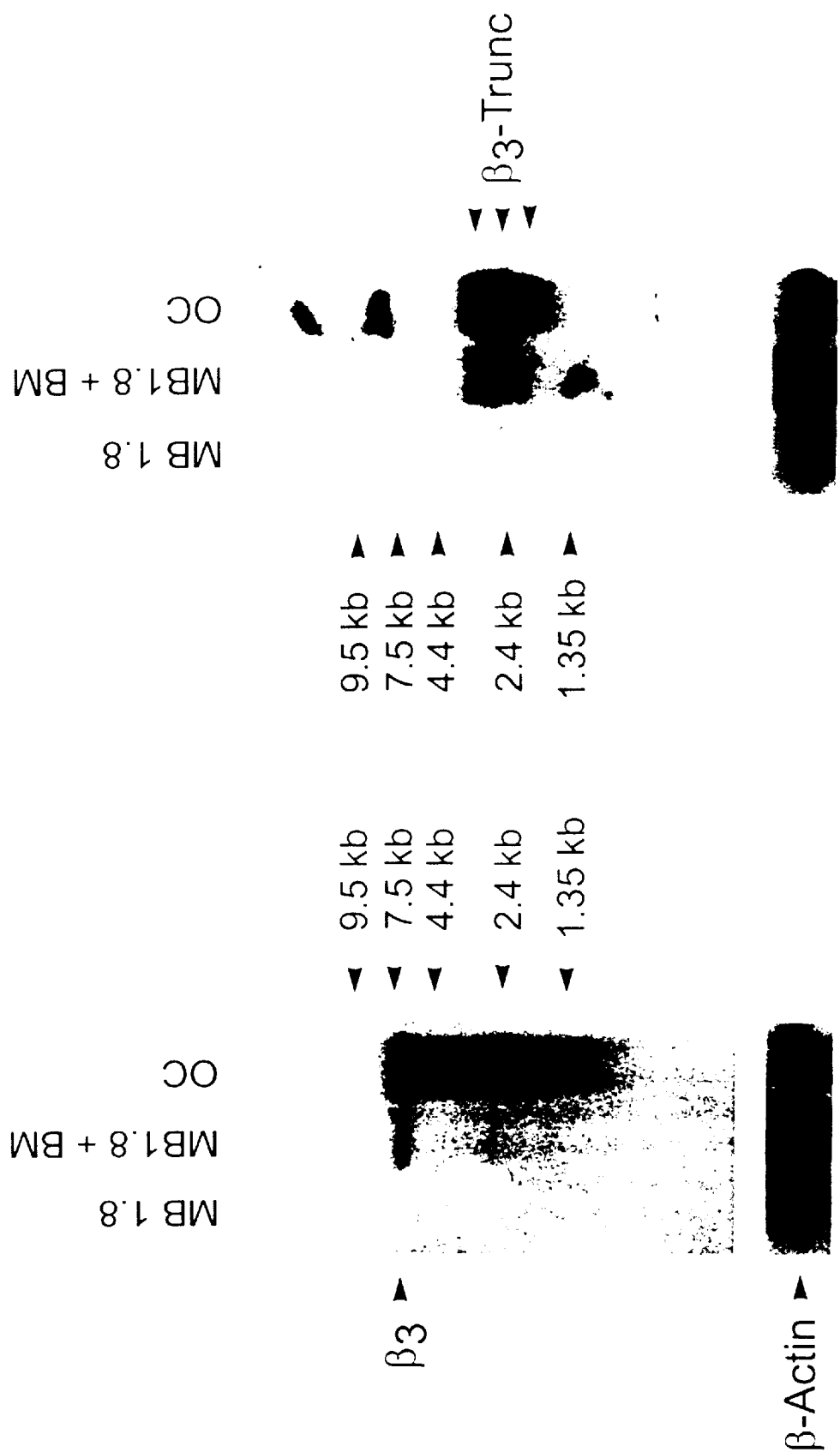

MOUSE INTEGRIN SUBUNITS

This is a division of application Ser. No. 08/960,387 filed Oct. 29, 1997, now U.S. Pat. No. 5,895,754, divisional of application U.S. Ser. No. 08/700,253, filed Aug. 20, 1996, now abandoned, which claims priority from provisional appl. 60/033,020 filed Aug. 31, 1995.

DESCRIPTION OF THE INVENTION

This invention relates to a new mouse vitronectin receptor subunit β3 (β3-trunc), the full length mouse vitronectin receptor, their nucleic acids, and to assays using these receptors. Additionally this invention includes soluble integrins which lack transmembrane and cytoplasmic domains.

BACKGROUND OF THE INVENTION

Integrins are transmembrane glycoproteins that mediate cell-cell and cell-matrix interactions. They contain two subunits, α and β, which are joined in a non-covalent complex. There are numerous α and β subunits known. Alpha subunits show some homology with other alpha subunits and beta subunits tend to show homology with other beta subunits, however, the alpha subunits tend to be quite distinct from beta subunits.

Osteoclasts are the primary cells responsible for bone resorption. Osteoclasts migrate to the area of the bone to be absorbed, and then attach to the bone. Adhesion molecules, including integrins, are believed to be involved in the processes of migration and attachment.

Recent studies have shown that both mature osteoclasts and tissue culture generated osteoclast-like cells highly express the vitronectin integrin receptor $α_vβ3$. The $α_vβ3$ integrin receptor recognizes the tripeptide Arg-Gly-Asp (RGD), found in many bone matrix proteins, and thus is thought to be involved in the attachment processes. However, there is no direct evidence that $α_vβ3$ mediates osteoclast attachment to bone in vivo.

Partial sequence of the mouse β3 cDNA was previously reported by Cieutat, et al., 1993 *Biochem. Biophys. Res. Comm.* 193:771–778. Cieutat et al., cloned β3 from mouse kidney RNA using RT/PCR and human primers. This published sequence did not have the N-terminus and the last 4 amino acids at the C-terminus.

There are presently two types of screens for the $α_vβ3$ ligands as an inhibitor for bone resorption: a binding assay based on human recombinant $α_vβ3$ integrin and a functional assay based on rodent osteoclasts. To exclude the possibility of species-based potency differences in ligand interaction with the $α_vβ3$ integrin, it would be desirable to develop an assay which uses the β3 integrin subunit from a mouse osteoclast.

DETAILED DESCRIPTION OF THE INVENTION

This invention relates to the full length mouse β3 integrin subunit (β3), nucleic acids encoding it, and to processes for cloning it. Another aspect of this invention is a novel form of the β3 integrin subunit, referred to as β3-trunc, which lacks the transmembrane and cytoplasmic domains, to nucleic acids encoding it, and to processes for producing it. Another aspect of this invention is the use of these integrins in assays to identify novel compounds which inhibit the bone absorption process.

Yet another aspect of this invention is a soluble ligand-binding integrin which, like other soluble receptors, suppresses the interaction of the full length integrins with their ligands. The main signal transduction pathway mediated by the a membrane bound integrin is transduced through the cytoplasmic domain of the β subunit. A soluble receptor, which has an intact binding domain but lacks the cytoplasmic domain, will suppress or compete with the normal signals mediated by the wild type receptor.

BRIEF DESCRIPTION OF THE FIGS.

FIGS. 1A–1D are the complete sequence of the mouse β3 integrin (2.3 kb) cloned from a osteoclast cDNA library, SEQ ID NO:2. The "ATG" initiation codon begins at position 164 and both a "TAA" and a "TGA" stop codons are seen starting at position 2525.

FIGS. 2A–2E are the cDNA of the mouse β3-trunc, SEQ ID NO:1. The "ATG" initiation codon begins at position 164.

FIGS. 3A and 3B are the amino acid sequence of mouse β3-trunc SEQ ID NO:4. This sequence shows the corresponding amino acids, including untranslated regions. Asterisks denote stop codons. As shown in FIG. 5, the open reading frame begins with the "Met" at position 55, and ends with the "Ala" at position 782.

FIGS. 4A and 4B are the amino acid sequence of the full-length mouse β3. This sequence shows corresponding amino acids, including untranslated regions. Asterisks denote stop codons. As shown in FIG. 5, the open reading frame begins with the "Met" at position 55, and ends with the "Thr" at position 841.

FIGS. 5A–5C are an amino acid sequence comparison between the mouse full-length β3 (top line), SEQ ID NO:3, and the mouse β3-trunc (lower line), SEQ NO ID:4, FIGS. 6A and 6B are gels showing the expression of mouse full-length β3 and β3-trunc in osteoclast-like cells in the mouse co-culture system.

Figure 7:
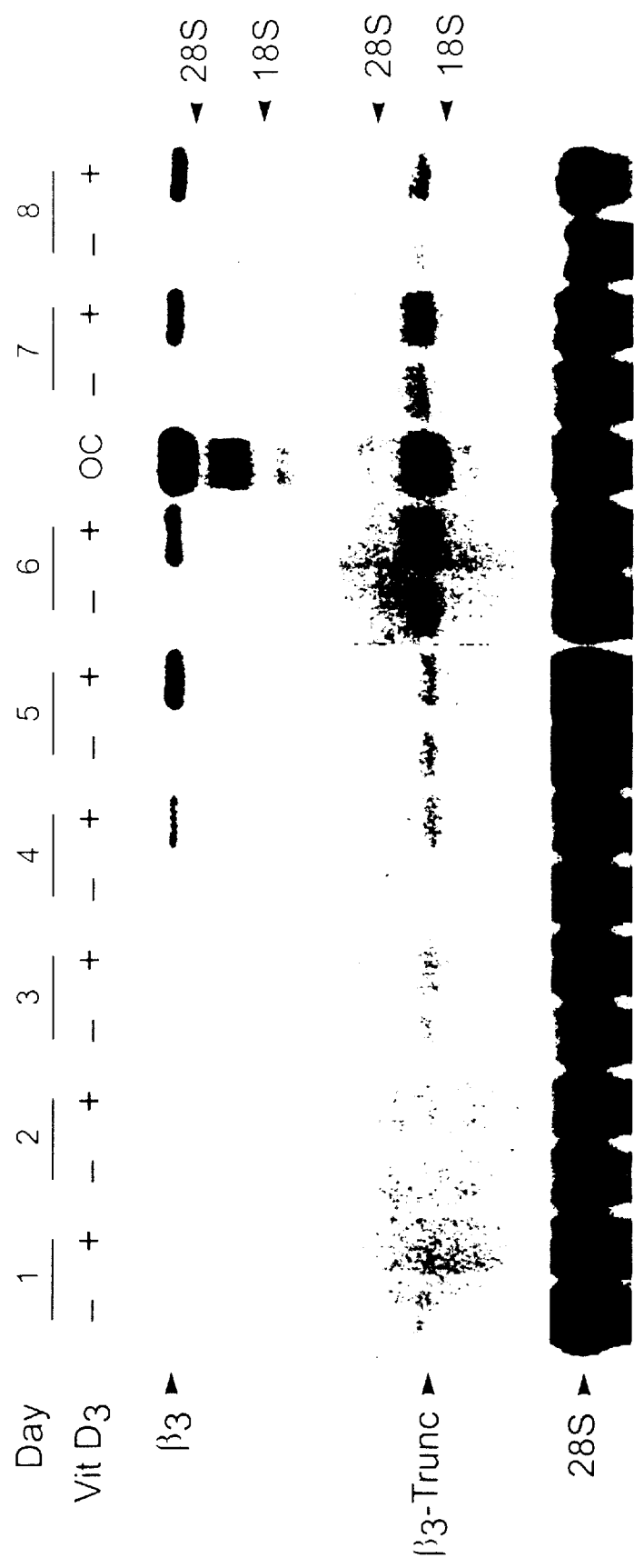

FIG. 7 are gels demonstrating the regulation of both β3 and β3-trunc by 1,25-dihydroxy Vitamin D3.

Figure 8:
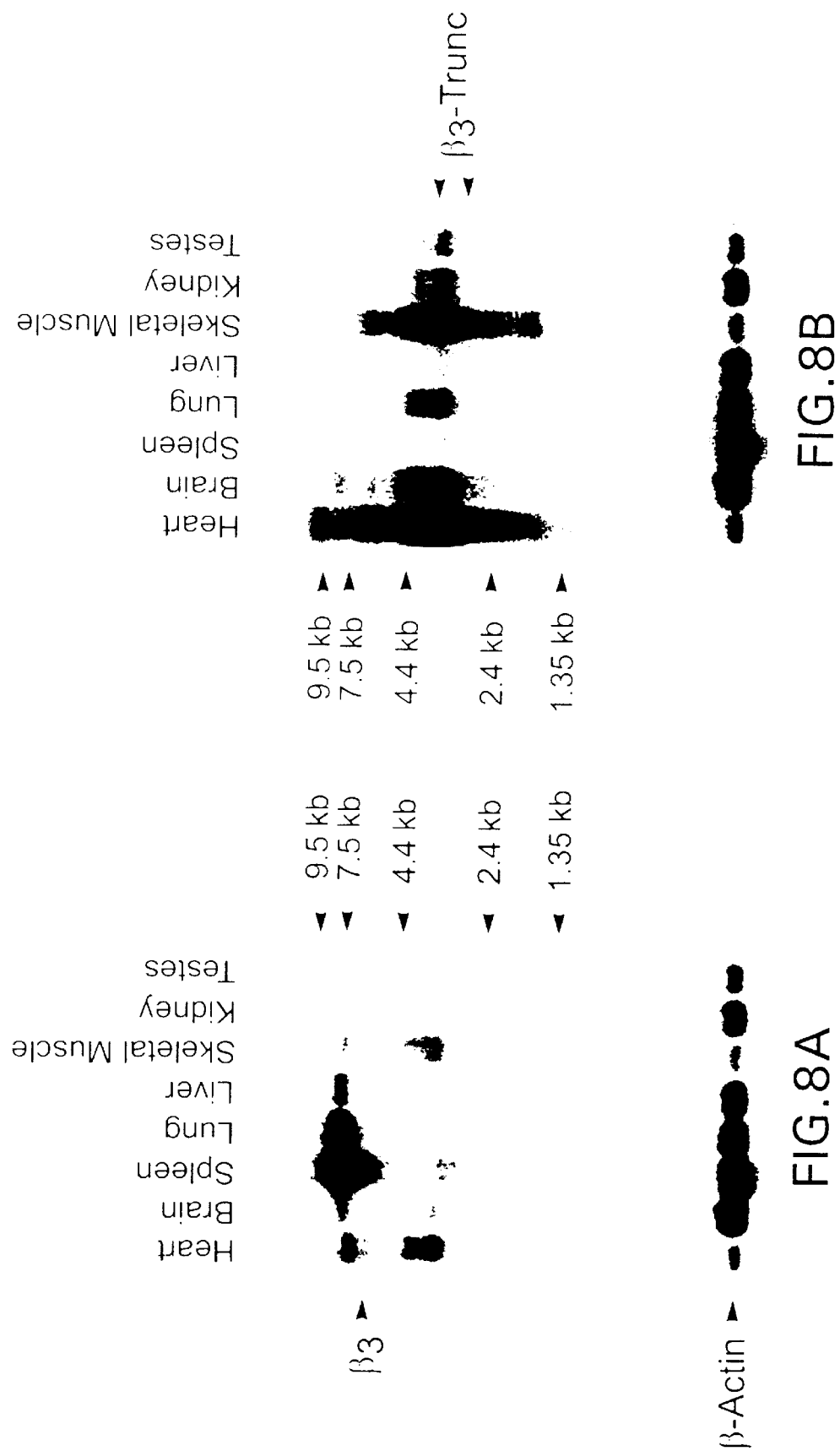

FIGS. 8A and 8B are gels showing the expression of β3 and β3-trunc in various tissues.

Figure 9:
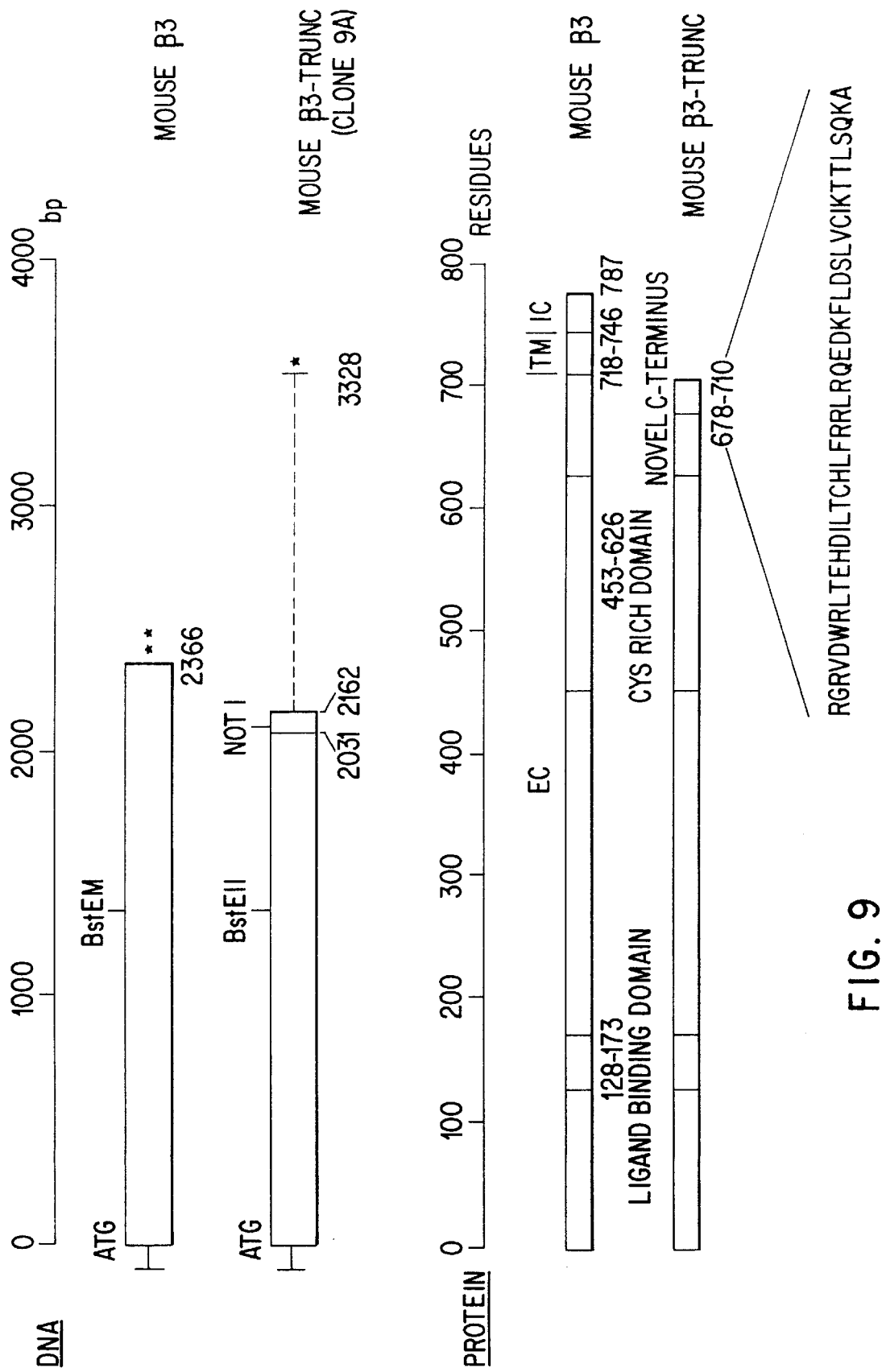

FIG. 9 are diagrams of the mouse β3 and β3-trunc genes and the proteins encoded.

As used in the specification and claims, the following definitions shall apply:

"Free from associated mouse nucleic acid"—physically separated from mouse nucleic acid (DNA or RNA) which either (i) mouse β3 nucleic acid or (ii) mouse β3-trunc nucleic acid. "Free from associated mouse DNA"—physically separated from mouse DNA which is not either (i) mouse DNA encoding β3 integrin or (ii) DNA encoding truncated β3 integrin. "Substantially pure"—a protein or nucleic acid is "substantially pure" when the amount of other protein or nucleic acid present in a sample is less than about 5% of the sample by weight.

Thus one aspect of this invention is nucleic acids which encode the full length mouse β3 integrin, said nucleic acid being free from associated mouse nucleic acid. Preferably the nucleic acid is a DNA. A preferred type of DNA is cDNA, and a particularly preferred cDNA is that shown in FIG. 1A–1D.

Partial sequence of the mouse β3 cDNA was previously reported by Cieutat, et al., 1993 *Biochem. Biophys. Res. Comm.* 193:771–778, which is hereby incorporated by reference. Cieutat et al cloned β3 from mouse kidney RNA using RT/PCR and human primers. This published sequence did not have the N-terminus and the last 4 amino acids at the C-terminus. One aspect of this invention comprises a complete sequence of the mouse β3 integrin (2.3 kb) cloned from a osteoclast cDNA library, free from associated mouse cDNA, or which is substantially pure. This is presented in FIG. 1. The sequence of β3 was derived from the cDNA sequence of clone 9A (from 5'-end to base 2028) and the PCR sequence of a fragment encoding the last 363 bases at the 3'-end.

Another aspect of this invention is the complete, full-length β3 peptide, free from associated mouse peptides, or substantially pure which is shown in FIG. 4A and 4B. Substantially pure mouse full-length β3 is another aspect of this invention.

Mouse β3 shows 86% homology with the human β3 at the DNA level, 90% overall homology in the amino acid sequence, 90% and 100% homology in the ligand binding domains (residues 109–171 and residues 204–229, respectively), 97% homology in the transmembrane domain and 100% identity in the cytoplasmic tail. This high homology is consistent with the quantitative similarity in the binding of ligands to human and mouse $\alpha_v\beta3$.

Another aspect of this invention are vectors which comprise the full length mouse β3 nucleic acids, preferably cDNA and to host cells transformed with these vectors. Preferred host cells are embryonic kidney cells. This invention also includes the method of making full length β3 by transforming a host cell with a vector comprising full length mouse β3 DNA and harvesting the β3 so produced.

Characterization of the Truncated Mouse β3 cDNA (β3-trunc)

Another aspect of this invention is nucleic acids which encode a truncated mouse β3 (β3-trunc) peptide, free from associated mouse nucleic acids, or which are substantially pure. A preferred form of β3-trunc DNA is cDNA; a particularly preferred cDNA is that shown in FIG. 2.

Another aspect of this invention is the β3-trunc peptide, free from associated mouse peptides, or substantially pure. This is shown in FIGS. 3A and 3B and FIG. 9. Mouse β3-trunc, which includes 5'-untranslated region (163 bp), 5'-coding region of the extracellular domain of β3 (up to base 2028 or residue 676) and a diversed 3'-coding region. Interestingly, the diversed 3'-coding region includes an in-frame addition of 43 amino acids, followed by a long 3'-untranslated sequence (1.2 kb). From homology analysis, this diversed 3'-sequence shows no significant homology with any known gene. The protein encoded by the β3-trunc gene contains the entire ligand binding and cysteine-rich domains, but lacks the transmembrane and cytoplasmic domains.

The expression of β3-trunc and its regulation in the co-culture-derived osteoclasts was investigated. Northern analysis of the co-culture, with either a 5'-probe or a 3'-specific ⊖3-trunc probe, reveals that the osteoblastic MB 1.8 cells do not express β3 or β3-trunc (see FIG. 6A and 6B). However, the expression of both forms is highly enriched in the partially purified preparation of osteoclasts from the co-culture. The 5'-probe hybridizes to a major mRNA product at 6.5 kb and several minor forms of 2–4 kb. The β3-trunc specific probe detects a major mRNA product at 3 kb and two minor mRNA products at 2 and 4 kb. Generation of osteoclasts in the co-culture system depends on the presence of 1,25-dihydroxy Vitamin D3 (1,25(OH)2D3). Both forms of β3 integrin were up-regulated by 1,25(OH) 2D3 treatment of the co-culture system as shown in FIG. 7.

Murine tissue distribution reveals different patterns of expression for β3 and β3-trunc. This is demonstrated in FIGS. 8A and 8D. Full length β3 is expressed in spleen>lung>liver, with a very minor amount of β3 messages (6.5kb) detected in other tissues. In contrast, β3-trunc (2–4 kb) messages are expressed in heart>skeletal muscle>brain>lung.

Since β3-trunc lacks the transmembrane and cytoplasmic domains, it can be considered a soluble ligand binding integrin. This represents the first such soluble integrin. Thus another aspect of this invention is an integrin which lacks the transmembrane and cytoplasmic domains. Such an integrin is able to circulate throughout the organism. Its physiological role appears to be suppression of the signaling pathway mediated by the full length β3 integrins interaction with their ligands. Integrin-ligand signals are generally transmitted to the cytoplasm by a mechanism involving the cytoplasmic domain. However, when a ligand binds to β3-trunc, which lacks such a domain, the signal would not reach the cytoplasm. Therefore, the soluble ligands can act as negative regulators, tying up ligand without signaling the cell.

Assays

Another aspect of this invention are novel assays. The novel assays of this invention are to identify inhibitors of human $\alpha_v\beta3$ receptors. Such inhibitors would be useful in a variety of disease conditions including diseases associated with bone resorption such as osteoporosis. Generally, potential inhibitors are first screened for their ability to bind to recombinant human $\alpha_v\beta3$ receptors using an assay such as the one set forth in Example 2. Further in vitro testing of the potential inhibitor, however, generally occurs using mouse or other rodent cell systems. It is not uncommon for the same potential inhibitor to display different responses in the two systems, and until now the investigator would not be able to determine if the differences were due to the effect of the different species' receptors or to actual in vitro activity.

Thus, in one aspect of this invention, a potential inhibitor to osteoclast formation is placed into contact with either mouse full length β3 or mouse β3-trunc, and its ability to bind is measured. The binding may be measured by any known means, such as by measuring the displacement of a compound known to bind to β3, such as echistatin. This information can be used to better assess the activity of the potential inhibitor in an in vitro assay.

By means of example only, if a potential inhibitory compound were found to bind well to human $\alpha_v\beta3$ in the recombinant $\alpha_v\beta3$ assay, but exhibited less inhibitory activity than expected in the mouse in vitro assay, one could determine whether the decrease in expected activity was due to the compound's inability to bind efficiently to the mouse integrin or whether the decreased activity was a true reflection of the compound's in vitro activity, by performing a mouse β3 or β3-trunc assay.

The following non-limiting Examples are presented to further illustrate the invention.

EXAMPLES

General Techniques

First-Strand cDNA synthesis kit and QuickPrep mRNA Purification Kit were from Pharmacia. Lamda ZAP II cloning kits were from Stratagene. Mouse tissue mRNA blots were purchased from Clontech. Hybond-N filters were from Amersham. Restriction enzymes were from various sources: BioLabs, Promega and Stratagene. Tissue culture media were from Gibco. Fetal bovine serum was obtained from JRH Bioscience.

EXAMPLE 1

Strategy for Isolating cDNA Clones for the Mouse ⊖3 Subunit

Generation of a Mouse ⊖3 cDNA Probe (mβ3 Probe)

This probe was generated using the following degenerate oligonucleotide primers:

5'-primer:
CCA AGC TTG AC(A/C) T(G/C)T ACT A(C/T)C T(G/T)A TGG A SEQ ID NO:5

3'-primer:
CCC TCG AGA A(A/G)T (C/T)GT CGC A(C/T)T CGC A(A/G)T A SEQ ID NO :6

The primers were designed based on a sequence which is highly conserved among all integrin β subunits (Ramaswamy & Hemler, 1990, *EMBO J.* 9: 1561–1568, which is incorporated by reference). Using polymerase chain reaction, a cDNA fragment of the ⊖3 subunit was cloned from a cDNA library prepared from mouse osteoclasts. The identity of this m⊖3 probe was confirmed by sequence analysis to be homologous to the published human β3 sequence (Frachet et al., 1990 *Mol. Biol. Rep.* 14:27–33, which is hereby incorporated by reference.).

Construction of a λZAP Mouse Osteoclast cDNA Library (λZAP-OC)

The cDNA library was constructed from 5 µg polyA(+) RNA prepared from osteoclasts, which were generated from a co-culture of osteoblastic MB 1.8 cells and mouse bone marrow cells in the presence of 1,25-dihydroxy Vitamin D3 (1,25(OH)2D3). Methods for generation and isolation of mouse osteoclasts from culture were performed as described by Tanaka, et al., 1991 *J. Bone Min. Res.* 6: S148, which is hereby incorporated by reference. The construction of this library was carried out according the instructions provided by the manufacturer, Stratagene (Lambda ZAP II Cloning Kits—236611). Random pd(N)6 primers were used for the first strand cDNA synthesis.

Screening for Mouse β3 clones

Mouse β3 CDNA clones were isolated by screening the primary λZAP-OC library (0.5×10⁶ pfu), using the mβ3 probe. Sixteen positive clones were isolated and rescued into pBluescipt phagemid according to the manufacturer's protocol (Stratagene). These clones were initially characterized by restriction digestion with EcoRI to estimate the size of cDNA inserts. Clone 9A was found to be the largest (3.5 Kb) and was subsequently characterized by sequence analysis.

Cloning of 3'-cDNA Fragment of Mouse β3 by PCR

Clone 9A encodes for the entire sequence of mouse β3-trunc, which lacks only 121 amino acids (363 bp) from the expected C-terminus of β3-full, based on the published human β3 sequence. Therefore, the rest of the 3'-cDNA fragment was cloned by PCR. The following primers were used:

5'-primer (from BstEII site of clone 9A):
TAA GGA CAG CCT CAC CGT CCA GGT SEQ ID NO:7

3'-primer (based on the human sequence):
TCA TTA AGT CCT CGG TAC GTG ATA TTG GTG SEQ ID NO:8

Full length mouse β3 cDNA was then constructed by ligating at the BstEII site between the clone 9A-derived 5'-fragment and the PCR clone-derived 3'-fragment.

RNA isolation and Northern blot analysis

Total cellular RNA was isolated by guanidine isothiocyanate and phenol extraction (Chomczynski & Sacchi, 1987, *Anal. Biochem.* 162:156–159.). Ten µg of total RNA was separated using formaldehyde-agarose gel electrophoresis, followed by transfer onto nylon filters (Hybond-N; Amersham). Poly A(+) RNA was prepared using QuickPrep mRNA Purification Kit (Pharmacia). Mouse tissue blots were purchased from Clontech. Mouse β3 specific probe was generated from the 5'-fragment of clone 9A using the EcoRI and BstEII sites. This probe can recognize both β3 full length and β3-trunc. Mouse β3-trunc specific probe was generated from the 3'-fragment of clone 9A using the Not I and EcoRI sites. Hybridizations were performed in 40% formamide, 5×SSC, 0.1% SDS, 0.1% ficoll, 0.1% polyvinylpyrolidone, 0.1% BSA and 200 mg/ml sonicated salmon sperm DNA at 42° C., overnight, and washed two times (30 min) at 55° C. in 0.1×SSC and 0.1% SDS. The filters were dried and exposed to XAR-2 films (Eastman Kodak, Rochester, N.Y.).

EXAMPLE 2

Osteoclast Formation Assay

Osteoclast formation was determined using the mouse bone marrow-derived osteoblast co-culture system, as described by Takahashi, et al., 1988 In this assay, an osteoblastic cell line (MB 1.8), established from neonatal mouse calvaria, were plated in 24-well culture dishes, at 10,000 cells per cm² in α-MEM containing 10% fetal bovine serum and 10 nM $1,25(OH)_2D_3$. Balb/C male mice (six weeks old) were sacrificed under CO2, and tibiae and femors were aseptically removed. The bone ends were cut off with scissors and the marrow cavity was flushed with 1 ml α-MEM by using a 27G needle. The bone marrow cells were then filtered through 70 µm nylon mesh. Cells were centrifuged for 7 min. at 300×g and washed once with α-MEM and finally resuspended and aliquoted at 25,000 cells/cm² onto the MB 1.8 cells in the 24-well culture dishes. Medium with 10 nM 1,25(OH)2D3 was replaced every two days. Potential inhibitors of osteoclast formation were added to the cultures at day 2 and at day 4. After 7 days, the cultures were fixed and stained for Tartrate-resistance acid phosphatase (Trap) activity, essentially as described in Takahashi, et al., 1988. The formation of osteoclasts in this co-culture was quantitated as the number of multinucleated Trap(+) cells (with three or more nuclei) per well of a 24-well tissue culture plate.

Recombinant Expression of Functional Human Integrin $α_vβ3$ cDNAs for human $α_v$ and human $⊖_3$ were cloned into pR135 and pCDNAI-neo expression vectors, both of which use the CMV promoter but contain hygromycin or neomycin resistance markers, respectively. Using these selection markers, we established a stable human embryonic kidney 293 cell line that stably expresses high levels of recombinant human $α_vβ3$ was established. Surface expression of the receptor in this $^{293}(α_vβ3)$ cell line were characterized using northern analysis, surface radioiodination followed by immunoprecipitation. In addition, the number of $α_vβ3$ integrin receptors on the cell surface was estimated to be $1×10^6$ receptor per cell, based on specific binding of $α_vβ3$ to radio-iodinated echistatin.

Using the $^{293}(α_vβ3)$ cell line, two different assays were developed for screening inhibitors of the integrin $α_vβ3$: echistatin binding assay (EIB) and vitronectin cell attachment assay (VNADIN), below.

Echistatin Binding Assay (EIB)

The membrane fraction of $^{293}(α_vβ3)$ was solubilized in 100 mM octyl glucoside and the membrane protein extract is used in radio-iodinated echistatin binding. Binding buffer is 1% bovine serum albumin, 50 mM Tris-HCl (pH 7.2), 150 mM NaCl, 1 mM $CaCl_2$ and 1 mM $MgCl_2$. Membrane extract is incubated with radioiodinated echistatin (50,000 cpm), in the absence (total binding) or in the presence of unlabeled echistatin (specific binding) or in the presence of test compounds. Incubation period is 1 hour at room temperature. Specific echistatin bound proteins are filtered through a membrane using a Skatron Cell Harvester system.

Vitronectin Cell Attachment Assay (VNADIN)

96-well plates are coated with human vitronectin 293 ($\alpha_v\beta 3$) cells are lifted in trypsin/EDTA and washed in serum-free media. Cells are resuspended in attachment medium (Hank's balance salt containing BSA (1mg/ml) and $CaC_2$ (2mM). Cells are then allowed to attach to vitronectin-coated wells for 1 hr at 37° C., in the absence (total attachment) or in the presence of tested compounds. Non-adhered cells are then removed by gently washing the wells with phosphate buffered saline.

The number of adhered cells can be quantitated by determining the relative levels of glucosaminidase activity overnight. The enzyme substrate solution is 3.75 mM p-nitrophenyl-N-acetyl-$\beta$-D-glucosaminide in 0.1 M citrate buffer (pH 5.0) and 0.25% Triton X-100. The plates are incubated in the dark, room temperature, overnight. The color reaction is then developed by addition of 50 mM glycine, 5 mM EDTA at pH 10.5 Absorbance at O.D. 405 nm is determined and the number of cells can be quantitated using a standard curve of cells.

Assays Using Mouse $\beta 3$

Essentially the same procedure is followed as described above to create a human embryonic kidney 293 cell line expressing either full-length mouse $\beta 3$ or mouse $\beta 3$ trunc. The EIB and/or VNADIN assays are then performed substantially as described, substituting the mouse $\beta 3$ or mouse $\beta 3$-trunc expressing cells.

What is claimed is:

1. An isolated full-length mouse β3 integrin, which consists of SEQ ID NO:3, said mouse β3 integrin being free from associated mouse proteins.

2. An isolated full-length mouse β3 integrin according to claim 1, which is substantially pure.

3. An isolated mouse β3-trunc integrin, which consists of SEQ ID NO:4, said mouse β3-trunc integrin being free from associated mouse proteins.

4. A method to determine the ability of a compound to bind to a full-length β3 or β3-trunc integrin which consists of SEQ ID NO: 3 or SEQ ID NO :4, respectively, comprising contacting the compound with said full length β3 or β3-trunc and measuring the resultant binding.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2530 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
ATAACAATTT CACACAGGAA ACAGCTATGA CCATGATTAC GCCAAGCTCG AAATTAACCC        60

TCACTAAAGG GAACAAAAGC TGGAGCTCCA CCGGTGGCGG CCGCTCTAGA ACTAGTGGAT       120

CCCCCGGGCT GCAGGAATTC GCGCCGTCGA CGCGGCGGAC AGGATGCGAG CGCAGTGGCC       180

GGGACAACTC TGGGCCGCTC TGCTGGCGCT GGGGGCGCTG GCGGGCGTTG TTGTTGGAGA       240

GTCCAACATC TGTACCACAC GAGGCGTGAA CTCCTGCCAG CAGTGTCTGG CTGTGAGTCC       300

TGTGTGTGCC TGGTGCTCAG ATGAGACTTT GTCTCAGGGC TCACCCCGAT GTAACCTGAA       360

GGAGAACCTG CTGAAGGACA ATTGTGCTCC AGAGTCTATT GAGTTCCCAG TCAGTGAGGC       420

CCAGATCCTG GAGGCTAGGC CACTCAGCAG CAAGGGCTCT GGAAGCAGCG CCCAGATCAC       480

TCAAGTCAGC CCTCAGAGGA TTGCCCTTCG ACTACGGCCA GATGATTCGA AGATCTTCTC       540

ACTTCAAGTG CGGCAGGTGG AGGATTACCC CGTGGACATC TACTACTTGA TGGACCTGTC       600

TTTCTCCATG AAGGATGATC TGTCCAGCAT CCAGACCCTG GGTACCAAGT TGGCCTCTCA       660

GATGCGCAAG CTTACTAGCA ACCTTCGGAT TGGCTTTGGG GCCTTCGTGG ACAAGCCTGT       720

ATCGCCGTAC ATGTACATCT CCCCACCACA GGCAATCAAA AACCCCTGTT ACAATATGAA       780

GAATGCCTGC TTGCCCATGT TTGGCTACAA ACACGTGCTG ACGCTAACCG ACCAGGTGTC       840

CCGCTTCAAT GAAGAAGTGA AGAAACAGAG CGTGTCCCGT AATCGAGATG CCCCAGAGGG       900

CGGCTTTGAC GCCATCATGC AGGCTACAGT ATGTGATGAA AAAATTGGCT GGAGGAATGA       960

CGCATCCCAT TTGCTAGTGT TTACCACGGA TGCCAAGACC CATATTGCCC TGGATGGAAG      1020

ACTGGCAGGC ATTGTCCTGC CCAATGATGG GCACTGTCAC ATTGGCACCG ACAACCACTA      1080

CTCTGCCTCC ACTACCATGG ACTACCCATC TCTGGGGCTG ATGACTGAGA AACTATCCCA      1140

GAAAAACATT AACTTGATCT TTGCAGTGAC TGAAAATGTC GTCAGCCTTT ACCAGAATTA      1200
```

-continued

```
TAGTGAGCTC ATTCCTGGGA CCACAGTGGG AGTCCTGTCT GATGACTCAA GCAACGTCCT      1260

CCAGCTGATT GTTGATGCTT ACGGGAAAAT CCGCTCTAAA GTGGAGCTGG AAGTACGTGA      1320

CCTGCCGGAA GAACTGTCAC TGTCCTTCAA TGCCACCTGC CTCAACAACG AGGTTATCCC      1380

GGGCCTCAAG TCTTGTGTGG GCCGCAAGAT TGGAGACACG GTGAGCTTTA GTATCGAGGC      1440

CAAGGTGCGT GGCTGCCCCC AGGAGAAGGA GCAGTCTTTC ACTATCAAGC CTGTGGGCTT      1500

TAAGGACAGC CTCACCGTCC AGGTGACCTT CGACTGTGAC TGTGCCTGCC AGGCCTTTGC      1560

CCAGCCTTCC AGCCCACGCT GCAACAATGG GAACGGGACT TTTGAGTGTG GGGTGTGCCG      1620

CTGTGACCAG GCTGGCTGG GGTCCATGTG TGAGTGCTCT GAGGAGGATT ACCGACCCTC       1680

TCAGCAGGAA GAGTGCAGCC CCAAGGAGGG CCAGCCCATC TGCAGCCAGC GGGGAGAGTG      1740

CCTCTGTGGC CAGTGTGTCT GCCATAGCAG CGACTTCGGC AAGATCACTG GCAAGTACCA      1800

TGAGTGCGAT GACTTCTCCT GCGTCCGCTA CAAAGGGGA ATGTGTTCCG GCCATGGGCA       1860

ATGTAACTGT GGGGACTGCG TGTGTGACTC GGACTGGACT GGCTACTACT GCAACTGTAC      1920

TACACGCACT GACACCTGCA TGTCCACCAA TGGGCTGCTG TGCAGCGGCC GGGGCAACTG      1980

CGAGTGCGGC AGCTGTGTGT GCGTCCAGCC AGGCTCCTAT GGAGACACCT GTGAGAAGTG      2040

CCCCACCTGC CCAGATGCCT GCTCCTTTAA GAAGGAGTGT GTGGAGTGTA AGAAGTTCAA      2100

CCGGGGAACG CTCCATGAAG AAAACACCTG CAGCCGCTAC TGCCGGGATG ACATCGAGCA      2160

GGTGAAAGAG CTGACGGATA CTGGCAAAAA CGCCGTGAAT TGTACCTACA AGAACGAGGA      2220

TGACTGTGTC GTCAGATTCC AGTACTACGA AGACACCAGT GGGAGGGCAG TCCTCTATGT      2280

GGTGGAAGAG CCTGAGTGTC CCAAGGGTCC TGATATCCTG GTGGTACTGC TGTCAGTGAT      2340

GGGGGCCATC CTGCTCATTG GCCTTGCTAC TCTGCTCATC TGGAAGCTAC TCATCACCAT      2400

CCATGACCGG AAGGAATTTG CTAAATTTGA GGAAGAACGA GCCAGAGCTA AGTGGGACAC      2460

AGCAAACAAC CCGCTGTATA AGAGGCCAC CTCCACCTTC ACCAATATCA CGTACCGAGG       2520

AACTTAATGA                                                            2530
```

(2) INFORMATION FOR SEQ ID NO:2:

(i) SEQUENCE CHARACTERISTICS:
        (A) LENGTH: 3517 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
ATAACAATTT CACACAGGAA ACAGCTATGA CCATGATTAC GCCAAGCTCG AAATTAACCC        60

TCACTAAAGG GAACAAAAGC TGGAGCTCCA CCGGTGGCGG CCGCTCTAGA ACTAGTGGAT       120

CCCCCGGGCT GCAGGAATTC GCGCCGTCGA CGCGGCGGAC AGGATGCGAG CGCAGTGGCC       180

GGGACAACTC TGGGCCGCTC TGCTGGCGCT GGGGGCGCTG GCGGGCGTTG TTGTTGGAGA       240

GTCCAACATC TGTACCACAC GAGGCGTGAA CTCCTGCCAG CAGTGTCTGG CTGTGAGTCC       300

TGTGTGTGCC TGGTGCTCAG ATGAGACTTT GTCTCAGGGC TCACCCCGAT GTAACCTGAA       360

GGAGAACCTG CTGAAGGACA ATTGTGCTCC AGAGTCTATT GAGTTCCCAG TCAGTGAGGC       420

CCAGATCCTG GAGGCTAGGC CACTCAGCAG CAAGGGCTCT GGAAGCAGCG CCCAGATCAC       480

TCAAGTCAGC CCTCAGAGGA TTGCCCTTCG ACTACGGCCA GATGATTCGA AGATCTTCTC       540

ACTTCAAGTG CGGCAGGTGG AGGATTACCC CGTGGACATC TACTACTTGA TGGACCTGTC       600
```

-continued

```
TTTCTCCATG AAGGATGATC TGTCCAGCAT CCAGACCCTG GGTACCAAGT TGGCCTCTCA      660
GATGCGCAAG CTTACTAGCA ACCTTCGGAT TGGCTTTGGG GCCTTCGTGG ACAAGCCTGT      720
ATCGCCGTAC ATGTACATCT CCCCACCACA GGCAATCAAA AACCCCTGTT ACAATATGAA      780
GAATGCCTGC TTGCCCATGT TTGGCTACAA ACACGTGCTG ACGCTAACCG ACCAGGTGTC      840
CCGCTTCAAT GAAGAAGTGA AGAAACAGAG CGTGTCCCGT AATCGAGATG CCCCAGAGGG      900
CGGCTTTGAC GCCATCATGC AGGCTACAGT ATGTGATGAA AAAATTGGCT GGAGGAATGA      960
CGCATCCCAT TTGCTAGTGT TTACCACGGA TGCCAAGACC CATATTGCCC TGGATGGAAG     1020
ACTGGCAGGC ATTGTCCTGC CCAATGATGG GCACTGTCAC ATTGGCACCG ACAACCACTA     1080
CTCTGCCTCC ACTACCATGG ACTACCCATC TCTGGGGCTG ATGACTGAGA AACTATCCCA     1140
GAAAAACATT AACTTGATCT TTGCAGTGAC TGAAAATGTC GTCAGCCTTT ACCAGAATTA     1200
TAGTGAGCTC ATTCCTGGGA CCACAGTGGG AGTCCTGTCT GATGACTCAA GCAACGTCCT     1260
CCAGCTGATT GTTGATGCTT ACGGGAAAAT CCGCTCTAAA GTGGAGCTGG AAGTACGTGA     1320
CCTGCCGGAA GAACTGTCAC TGTCCTTCAA TGCCACCTGC CTCAACAACG AGGTTATCCC     1380
GGGCCTCAAG TCTTGTGTGG GCCGCAAGAT TGGAGACACG GTGAGCTTTA GTATCGAGGC     1440
CAAGGTGCGT GGCTGCCCCC AGGAGAAGGA GCAGTCTTTC ACTATCAAGC TGTGGGCTT     1500
TAAGGACAGC CTCACCGTCC AGGTGACCTT CGACTGTGAC TGTGCCTGCC AGGCCTTTGC     1560
CCAGCCTTCC AGCCCACGCT GCAACAATGG GAACGGGACT TTTGAGTGTG GGGTGTGCCG     1620
CTGTGACCAG GGCTGGCTGG GGTCCATGTG TGAGTGCTCT GAGGAGGATT ACCGACCCTC     1680
TCAGCAGGAA GAGTGCAGCC CCAAGGAGGG CCAGCCCATC TGCAGCCAGC GGGGAGAGTG     1740
CCTCTGTGGC CAGTGTGTCT GCCATAGCAG CGACTTCGGC AAGATCACTG GCAAGTACTG     1800
TGAGTGCGAT GACTTCTCCT GCGTCCGCTA CAAAGGGGAG ATGTGTTCCG GCCATGGGAC     1860
ATGTAACTGT GGGGACTGCG TGTGTGACTC GGACTGGACT GGCTACTACT GCAACTGTAC     1920
TACACGCACT GACACCTGCA TGTCCACCAA TGGGCTGCTG TGCAGCGGCC GGGGCAACTG     1980
CGAGTGCGGC AGCTGTGTGT GCGTCCAGCC AGGCTCCTAT GGAGACACCT GTGAGAAGTG     2040
CCCCACCTGC CCAGATGCCT GCTCCTTTAA GAAGGAGTGT GTGGAGTGTA AGAAGTTCAA     2100
CCGGGGAACG CTCCATGAAG AAAACACCTG CAGCCGCTAC TGCCGGGATG ACATCGAGCA     2160
GGTGAAAGAG CTGACGGATA CTGGCAAAAA CGCCCGCGGC CGCGTCGACT GGAGACTCAC     2220
GGAGCATGAC ATACTCACCT GTCACCTATT TAGAAGACTG AGGCAGGAAG ATAAGTTTCT     2280
GGACAGCCTA GTCTGCATAA AGACCACCCT GTCTCAAAAA GCATAAAAGG GGCGTGGTGA     2340
ATGCCTGCTT AGCATATAGC CCTTGGTTGC AGGTAGTGCA GTACATAGGT GAAATCTGCC     2400
GCTACCTGCT GAGGCAGCCG GTTCGCGACG TGGAGCAGCG ACACCGCGTG CGCCTGGCCG     2460
CGGGTAATGG GCTGCGGCCA GCCATCTGGG AGGAGTTCAC GCAGCGCTTC GGTGTGCCAC     2520
AGATCGGCGA GTTCTACGGC GCTACCGAGT GCAACTGAGC ATTGCCAACA TGGACGGCAA     2580
GGTTCGCAGC TGTGGGGTGC AGGCGGGCGC TGTCGGTTTC CTACGACACA AGAGCCTTCA     2640
GGCCGCCCTC ACCGCCGCTG TATTCACCCT AGGTCGGCTC CTGCGGCTTC AACAGCCGTA     2700
TCCTCACGCA TGTGTACCCC ATCCGTCTGG TCAAGGTCAA TGAGGACACG ATGGAGCCAC     2760
TGCGGGACTC CGAGGGCCTC TGCATCCCGT GCCAGCCCGG TGAGTGTGGC CCTTGCCTGG     2820
TGCCTCGGGG AGCTAGAGTC CCCACGGCCC CCACACCCAC TCAGCTTGAG TGTCAACCTC     2880
CTTCCAGGGG AACCCGGCCT TTCGTGGGCC AGATCAACCA GCAGGACCCT CTGCGGCGTT     2940
```

```
TCGATGGTTA TGTTAGTGAC AGTGCCACCA ACAAGAAGAT TGCCCACAGC GTTTTCCGAA    3000

AGGCGATACG GCCTACCTCT CAGGTGCGGA CGCTCGTGGT CGTGGCTGGG CTGGCTGTCA    3060

GACTGCAAAG CCCGGTCCCA TCTGCCCCTC TTCCCTGCAG GTGACGTGCT AGTGATGGAC    3120

GAGCTGGGCT ACATGTATTT CCGTGACCGC AGCGGGACA CCTTCCGCTG GCGCGGGAGA     3180

ACGTGTCCAA CCACGGAGGT GAAGCCGGTG CTGAGCCGCC TACTGGGCCA GACGGACGTG    3240

GCTGTGTATG GGGTGGCTGT GCAGGCAAGC TGGGACACA GGGTGGTTGT GGTGTGCAGG     3300

AGCCCCATGG AGTCCATCCA GAAGGGACCT GCAGGTACAG TACCCGTGGG CCATGCACAA    3360

GGTGGAGAAC TGTGTTGCTG CTGACTGGGT GGGCACTGGG TTGGGAATCC ATCCACATTC    3420

CTAATATTGA ACTTCAGTCT GGGGGACCCC TTCTCAGGAT CAGAAGGCTG AAAACAGGTC    3480

GACGCCGCCC GGAATTCGAT ATCAAGCTTA TCGATCC                             3517
```

(2) INFORMATION FOR SEQ ID NO:3:

(i) SEQUENCE CHARACTERISTICS:
        (A) LENGTH: 1152 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:3:

```
Gln Phe His Thr Gly Asn Ser Tyr Asp His Asp Tyr Ala Lys Leu Gl
1               5                   10                  15

Ile Asn Pro His Arg Glu Gln Lys Leu Glu Leu His Arg Trp Arg Pr
                20                  25                  30

Leu Asn Trp Ile Pro Arg Ala Ala Gly Ile Arg Ala Val Asp Ala Al
            35                  40                  45

Asp Arg Met Arg Ala Gln Trp Pro Gly Gln Leu Trp Ala Ala Leu Le
        50                  55                  60

Ala Leu Gly Ala Leu Ala Gly Val Val Gly Glu Ser Asn Ile Cy
65                  70                  75                  80

Thr Thr Arg Gly Val Asn Ser Cys Gln Gln Cys Leu Ala Val Ser Pr
                85                  90                  95

Val Cys Ala Trp Cys Ser Asp Glu Thr Leu Ser Gln Gly Ser Pro Ar
                100                 105                 110

Cys Asn Leu Lys Glu Asn Leu Leu Lys Asp Asn Cys Ala Pro Glu Se
            115                 120                 125

Ile Glu Phe Pro Val Ser Glu Ala Gln Ile Leu Glu Ala Arg Pro Le
        130                 135                 140

Ser Ser Lys Gly Ser Gly Ser Ser Ala Gln Ile Thr Gln Val Ser Pr
145                 150                 155                 160

Gln Arg Ile Ala Leu Arg Leu Arg Pro Asp Asp Ser Lys Ile Phe Se
                165                 170                 175

Leu Gln Val Arg Gln Val Glu Asp Tyr Pro Val Asp Ile Tyr Tyr Le
            180                 185                 190

Met Asp Leu Ser Phe Ser Met Lys Asp Asp Leu Ser Ser Ile Gln Th
        195                 200                 205

Leu Gly Thr Lys Leu Ala Ser Gln Met Arg Lys Leu Thr Ser Asn Le
    210                 215                 220

Arg Ile Gly Phe Gly Ala Phe Val Asp Lys Pro Val Ser Pro Tyr Me
225                 230                 235                 240

Tyr Ile Ser Pro Pro Gln Ala Ile Lys Asn Pro Cys Tyr Asn Met Ly
```

-continued

```
                  245                 250                 255
Asn Ala Cys Leu Pro Met Phe Gly Tyr Lys His Val Leu Thr Leu Th
                260                 265                 270
Asp Gln Val Ser Arg Phe Asn Glu Glu Val Lys Gln Ser Val Se
            275                 280                 285
Arg Asn Arg Asp Ala Pro Glu Gly Phe Asp Ala Ile Met Gln Al
        290                 295                 300
Thr Val Cys Asp Glu Lys Ile Gly Trp Arg Asn Asp Ala Ser His Le
305                 310                 315                 320
Leu Val Phe Thr Thr Asp Ala Lys Thr His Ile Ala Leu Asp Gly Ar
                325                 330                 335
Leu Ala Gly Ile Val Leu Pro Asn Asp Gly His Cys His Ile Gly Th
                340                 345                 350
Asp Asn His Tyr Ser Ala Ser Thr Thr Met Asp Tyr Pro Ser Leu Gl
                355                 360                 365
Leu Met Thr Glu Lys Leu Ser Gln Lys Asn Ile Asn Leu Ile Phe Al
            370                 375                 380
Val Thr Glu Asn Val Val Ser Leu Tyr Gln Asn Tyr Ser Glu Leu Il
385                 390                 395                 400
Pro Gly Thr Thr Val Gly Val Leu Ser Asp Asp Ser Ser Asn Val Le
                405                 410                 415
Gln Leu Ile Val Asp Ala Tyr Gly Lys Ile Arg Ser Lys Val Glu Le
                420                 425                 430
Glu Val Arg Asp Leu Pro Glu Glu Leu Ser Leu Ser Phe Asn Ala Th
            435                 440                 445
Cys Leu Asn Asn Glu Val Ile Pro Gly Leu Lys Ser Cys Val Gly Ar
        450                 455                 460
Lys Ile Gly Asp Thr Val Ser Phe Ser Ile Glu Ala Lys Val Arg Gl
465                 470                 475                 480
Cys Pro Gln Glu Lys Glu Gln Ser Phe Thr Ile Lys Pro Val Gly Ph
                485                 490                 495
Lys Asp Ser Leu Thr Val Gln Val Thr Phe Asp Cys Asp Cys Ala Cy
            500                 505                 510
Gln Ala Phe Ala Gln Pro Ser Ser Pro Arg Cys Asn Asn Gly Asn Gl
        515                 520                 525
Thr Phe Glu Cys Gly Val Cys Arg Cys Asp Gln Gly Trp Leu Gly Se
    530                 535                 540
Met Cys Glu Cys Ser Glu Glu Asp Tyr Arg Pro Ser Gln Gln Glu Gl
545                 550                 555                 560
Cys Ser Pro Lys Glu Gly Gln Pro Ile Cys Ser Gln Arg Gly Glu Cy
                565                 570                 575
Leu Cys Gly Gln Cys Val Cys His Ser Ser Asp Phe Gly Lys Ile Th
            580                 585                 590
Gly Lys Tyr Cys Glu Cys Asp Asp Phe Ser Cys Val Arg Tyr Lys Gl
        595                 600                 605
Glu Met Cys Ser Gly His Gly Gln Cys Asn Cys Gly Asp Cys Val Cy
    610                 615                 620
Asp Ser Asp Trp Thr Gly Tyr Tyr Cys Asn Cys Thr Thr Arg Thr As
625                 630                 635                 640
Thr Cys Met Ser Thr Asn Gly Leu Leu Cys Ser Gly Arg Gly Asn Cy
                645                 650                 655
Glu Cys Gly Ser Cys Val Cys Val Gln Pro Gly Ser Tyr Gly Asp Th
            660                 665                 670
```

-continued

```
Cys Glu Lys Cys Pro Thr Cys Pro Asp Ala Cys Ser Phe Lys Lys Gl
            675                 680                 685
Cys Val Glu Cys Lys Lys Phe Asn Arg Gly Thr Leu His Glu Glu As
        690                 695                 700
Thr Cys Ser Arg Tyr Cys Arg Asp Ile Glu Gln Val Lys Glu Le
705                 710                 715                 720
Thr Asp Thr Gly Lys Asn Ala Arg Gly Arg Val Asp Trp Arg Leu Th
                725                 730                 735
Glu His Asp Ile Leu Thr Cys His Leu Phe Arg Arg Leu Arg Gln Gl
            740                 745                 750
Asp Lys Phe Leu Asp Ser Leu Val Cys Ile Lys Thr Thr Leu Ser Gl
        755                 760                 765
Lys Ala Lys Gly Arg Gly Glu Cys Leu Leu Ser Ile Pro Leu Val Al
    770                 775                 780
Gly Ser Ala Val His Arg Asn Leu Pro Leu Ala Glu Ala Ala Gl
785                 790                 795                 800
Ser Arg Arg Gly Ala Ala Thr Pro Arg Ala Pro Gly Arg Gly Trp Al
                805                 810                 815
Ala Ala Ser His Leu Gly Gly Val His Ala Ala Leu Arg Cys Ala Th
            820                 825                 830
Asp Arg Arg Val Leu Arg Arg Tyr Arg Val Gln Leu Ser Ile Ala As
        835                 840                 845
Met Asp Gly Lys Val Arg Ser Cys Gly Val Gln Ala Gly Ala Val Gl
    850                 855                 860
Phe Leu Arg His Lys Ser Leu Gln Ala Ala Leu Thr Ala Ala Val Ph
865                 870                 875                 880
Thr Leu Gly Arg Leu Leu Arg Leu Gln Gln Pro Tyr Pro His Ala Cy
                885                 890                 895
Val Pro His Pro Ser Gly Gln Gly Gln Gly His Asp Gly Ala Thr Al
            900                 905                 910
Gly Leu Arg Gly Pro Leu His Pro Val Pro Ala Arg Val Trp Pro Le
        915                 920                 925
Pro Gly Ala Ser Gly Ser Ser Pro His Gly Pro His Thr His Ser Al
    930                 935                 940
Val Ser Thr Ser Phe Gln Gly Asn Pro Ala Phe Arg Gly Pro Asp Gl
945                 950                 955                 960
Pro Ala Gly Pro Ser Ala Ala Phe Arg Trp Leu Cys Gln Cys His Gl
                965                 970                 975
Gln Glu Asp Cys Pro Gln Arg Phe Pro Lys Gly Asp Thr Ala Tyr Le
            980                 985                 990
Ser Gly Ala Asp Ala Arg Gly Arg Gly Trp Ala Gly Cys Gln Thr Al
        995                 1000                1005
Lys Pro Gly Pro Ile Cys Pro Ser Ser Leu Gln Val Thr Cys Trp Th
    1010                1015                1020
Ser Trp Ala Thr Cys Ile Ser Val Thr Ala Ala Gly Thr Pro Ser Al
1025                1030                1035                1040
Gly Ala Gly Glu Arg Val Gln Pro Arg Arg Ser Arg Cys Ala Ala Ty
                1045                1050                1055
Trp Ala Arg Arg Thr Trp Leu Cys Met Gly Trp Leu Cys Arg Gln Al
            1060                1065                1070
Gly Asp Thr Gly Trp Leu Trp Cys Ala Gly Ala Pro Trp Ser Pro Se
        1075                1080                1085
```

```
Arg Arg Asp Leu Gln Val Gln Tyr Pro Trp Ala Met His Lys Val Gl
    1090                1095                1100
Asn Cys Val Ala Ala Asp Trp Val Gly Thr Gly Leu Gly Ile His Pr
1105                1110                1115                1120
His Ser Tyr Thr Ser Val Trp Gly Thr Pro Ser Gln Asp Gln Lys Al
                1125                1130                1135
Glu Asn Arg Ser Thr Pro Pro Gly Ile Arg Tyr Gln Ala Tyr Arg Se
            1140                1145                1150

(2) INFORMATION FOR SEQ ID NO:4:

(i) SEQUENCE CHARACTERISTICS:
        (A) LENGTH: 837 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:4:

Gln Phe His Thr Gly Asn Ser Tyr Asp His Asp Tyr Ala Lys Leu Gl
1               5                   10                  15
Ile Asn Pro His Arg Glu Gln Lys Leu Glu Leu His Arg Trp Arg Pr
            20                  25                  30
Leu Asn Trp Ile Pro Arg Ala Ala Gly Ile Arg Ala Val Asp Ala Al
        35                  40                  45
Asp Arg Met Arg Ala Gln Trp Pro Gly Gln Leu Trp Ala Ala Leu Le
    50                  55                  60
Ala Leu Gly Ala Leu Ala Gly Val Val Gly Glu Ser Asn Ile Cy
65                  70                  75                  80
Thr Thr Arg Gly Val Asn Ser Cys Gln Cys Leu Ala Val Ser Pr
                85                  90                  95
Val Cys Ala Trp Cys Ser Asp Glu Thr Leu Ser Gln Gly Ser Pro Ar
            100                 105                 110
Cys Asn Leu Lys Glu Asn Leu Leu Lys Asp Asn Cys Ala Pro Glu Se
        115                 120                 125
Ile Glu Phe Pro Val Ser Glu Ala Gln Ile Leu Glu Ala Arg Pro Le
    130                 135                 140
Ser Ser Lys Gly Ser Gly Ser Ser Ala Gln Ile Thr Gln Val Ser Pr
145                 150                 155                 160
Gln Arg Ile Ala Leu Arg Leu Arg Pro Asp Asp Ser Lys Ile Phe Se
                165                 170                 175
Leu Gln Val Arg Gln Val Glu Asp Tyr Pro Val Asp Ile Tyr Tyr Le
            180                 185                 190
Met Asp Leu Ser Phe Ser Met Lys Asp Asp Leu Ser Ser Ile Gln Th
        195                 200                 205
Leu Gly Thr Lys Leu Ala Ser Gln Met Arg Lys Leu Thr Ser Asn Le
    210                 215                 220
Arg Ile Gly Phe Gly Ala Phe Val Asp Lys Pro Val Ser Pro Tyr Me
225                 230                 235                 240
Tyr Ile Ser Pro Pro Gln Ala Ile Lys Asn Pro Cys Tyr Asn Met Ly
                245                 250                 255
Asn Ala Cys Leu Pro Met Phe Gly Tyr Lys His Val Leu Thr Leu Th
            260                 265                 270
Asp Gln Val Ser Arg Phe Asn Glu Glu Val Lys Lys Gln Ser Val Se
        275                 280                 285
```

-continued

```
Arg Asn Arg Asp Ala Pro Glu Gly Gly Phe Asp Ala Ile Met Gln Al
    290                 295                 300
Thr Val Cys Asp Glu Lys Ile Gly Trp Arg Asn Asp Ala Ser His Le
305                 310                 315                 320
Leu Val Phe Thr Thr Asp Ala Lys Thr His Ile Ala Leu Asp Gly Ar
                325                 330                 335
Leu Ala Gly Ile Val Leu Pro Asn Asp Gly His Cys His Ile Gly Th
            340                 345                 350
Asp Asn His Tyr Ser Ala Ser Thr Thr Met Asp Tyr Pro Ser Leu Gl
            355                 360                 365
Leu Met Thr Glu Lys Leu Ser Gln Lys Asn Ile Asn Leu Ile Phe Al
    370                 375                 380
Val Thr Glu Asn Val Val Ser Leu Tyr Gln Asn Tyr Ser Glu Leu Il
385                 390                 395                 400
Pro Gly Thr Thr Val Gly Val Leu Ser Asp Asp Ser Ser Asn Val Le
                405                 410                 415
Gln Leu Ile Val Asp Ala Tyr Gly Lys Ile Arg Ser Lys Val Glu Le
            420                 425                 430
Glu Val Arg Asp Leu Pro Glu Glu Leu Ser Leu Ser Phe Asn Ala Th
            435                 440                 445
Cys Leu Asn Asn Glu Val Ile Pro Gly Leu Lys Ser Cys Val Gly Ar
    450                 455                 460
Lys Ile Gly Asp Thr Val Ser Phe Ser Ile Glu Ala Lys Val Arg Gl
465                 470                 475                 480
Cys Pro Gln Glu Lys Glu Gln Ser Phe Thr Ile Lys Pro Val Gly Ph
                485                 490                 495
Lys Asp Ser Leu Thr Val Gln Val Thr Phe Asp Cys Asp Cys Ala Cy
            500                 505                 510
Gln Ala Phe Ala Gln Pro Ser Ser Pro Arg Cys Asn Asn Gly Asn Gl
            515                 520                 525
Thr Phe Glu Cys Gly Val Cys Arg Cys Asp Gln Gly Trp Leu Gly Se
    530                 535                 540
Met Cys Glu Cys Ser Glu Glu Asp Tyr Arg Pro Ser Gln Gln Glu Gl
545                 550                 555                 560
Cys Ser Pro Lys Glu Gly Gln Pro Ile Cys Ser Gln Arg Gly Glu Cy
                565                 570                 575
Leu Cys Gly Gln Cys Val Cys His Ser Ser Asp Phe Gly Lys Ile Th
            580                 585                 590
Gly Lys Tyr Cys Glu Cys Asp Asp Phe Ser Cys Val Arg Tyr Lys Gl
            595                 600                 605
Glu Met Cys Ser Gly His Gly Gln Cys Asn Cys Gly Asp Cys Val Cy
    610                 615                 620
Asp Ser Asp Trp Thr Gly Tyr Tyr Cys Asn Cys Thr Thr Arg Thr As
625                 630                 635                 640
Thr Cys Met Ser Thr Asn Gly Leu Leu Cys Ser Gly Arg Gly Asn Cy
                645                 650                 655
Glu Cys Gly Ser Cys Val Cys Val Gln Pro Gly Ser Tyr Gly Asp Th
            660                 665                 670
Cys Glu Lys Cys Pro Thr Cys Pro Asp Ala Cys Ser Phe Lys Lys Gl
            675                 680                 685
Cys Val Glu Cys Lys Lys Phe Asn Arg Gly Thr Leu His Glu Glu As
    690                 695                 700
Thr Cys Ser Arg Tyr Cys Arg Asp Asp Ile Glu Gln Val Lys Glu Le
```

```
705                 710                 715                 720
Thr Asp Thr Gly Lys Asn Ala Val Asn Cys Thr Tyr Lys Asn Glu As
                725                 730                 735
Asp Cys Val Val Arg Phe Gln Tyr Tyr Glu Asp Thr Ser Gly Arg Al
                740                 745                 750
Val Leu Tyr Val Val Glu Glu Pro Glu Cys Pro Lys Gly Pro Asp Il
                755                 760                 765
Leu Val Val Leu Leu Ser Val Met Gly Ala Ile Leu Leu Ile Gly Le
                770                 775                 780
Ala Thr Leu Leu Ile Trp Lys Leu Leu Ile Thr Ile His Asp Arg Ly
785                 790                 795                 800
Glu Phe Ala Lys Phe Glu Glu Arg Ala Arg Ala Lys Trp Asp Th
                805                 810                 815
Ala Asn Asn Pro Leu Tyr Lys Glu Ala Thr Ser Thr Phe Thr Asn Il
                820                 825                 830
Thr Tyr Arg Gly Thr
                835
```

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

CCAAGCTTGA CMTSTACTAY CTKATGGA                    28

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

CCCTCGAGAA RTYGTCGCAY TCGCARTA                    28

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

TAAGGACAGC CTCACCGTCC AGGT                        24

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

TCATTAAGTC CTCGGTACGT GATATTGGTG                    30